_United States Patent_ [19]

Ohata et al.

[11] 3,953,443

[45] Apr. 27, 1976

[54] METHOD FOR PRODUCING CYANURIC ACID

[75] Inventors: Yoichi Ohata; Masayuki Aihara, both of Toyama, Japan

[73] Assignee: Nissan Chemical Industries, Ltd., Tokyo, Japan

[22] Filed: Oct. 3, 1974

[21] Appl. No.: 511,918

[30] Foreign Application Priority Data

Oct. 5, 1973  Japan.............................. 48-111477

[52] U.S. Cl............................................. 260/248 A
[51] Int. Cl.²...................................... C07D 251/32
[58] Field of Search................................. 260/248 A

[56] References Cited
UNITED STATES PATENTS 3,172,886   3/1965   Christoffel et al.................. 260/248

_Primary Examiner_—John M. Ford
_Attorney, Agent, or Firm_—Haseltine, Lake & Waters

[57] ABSTRACT

A method of producing cyanuric acid with high yield, high thermal and production efficiency by heating urea in bulk wherein urea is supplied continuously under agitation into a reaction vessel, the heat transfer surface of which is maintained higher than 340°C, preferably between 340°C and 360°C, said vessel being equipped with an agitator and heated indirectly by the heat transfer medium, the reaction mixture is maintained permanently higher than 220°C, preferably between 220°C and 280°C, in any local point, and the reaction is carried out with a mean residence time of over 2.5 hours with heating and agitating.

4 Claims, No Drawings

METHOD FOR PRODUCING CYANURIC ACID

BACKGROUND OF THE INVENTION

This invention relates to a process for producing cyanuric acid from urea as starting material. So far, the process for producing cyanuric acid by heating urea has been known in the art, but the process has the disadvantage that, since the reaction product is changed once from a solid phase to a liquid phase and again to the solid phase to complete the reaction, it may be agglutinated or solidified and adhere to the heat transfer surface to retard agitation and obstruct the process of heat transfer, with the result that the product quality is lowered. According to the former proposals to obviate such defect, the reaction is carried out by using a kneading device equipped with vanes for powerful agitation and scraping of the heat transfer surface or a rotary kiln wherein the agglomerated intermediate product is caused to flow during the reaction. Alternatively, the reaction is carried out by stirring a self-flowing particulate material obtained by spraying molten urea to the particulate reaction product, or by heating the material on a belt or a drum or above the molten metal. Some of these known methods are used on an industrial scale. While the above defect may be overcome to some extent by these known methods, they have some merits and demerits and moreover the operational procedure is troublesome and highly complex.

SUMMARY OF THE INVENTION

It is the object of the present invention to provide a method for producing cyanuric acid from urea with a high yield and improved thermal and operating efficiency by using a simple apparatus. The present invention relates to a method for producing cyanuric acid by heating urea in bulk comprising supplying urea continuously under agitation into a reaction vessel, the heat transfer surface of which is maintained at a temperature higher than 340°C, preferably between 340°C and 360°C, said vessel being equipped with an agitator and heated indirectly by the heat transfer medium, maintaining the reaction mixture permanently at a temperature higher than 220°C, preferably between 220°C and 280°C, in any local point, and carrying out the reaction with a mean residence time of over 2.5 hours with heating and agitating. Further the reaction vessel used in the present invention is preferably a horizontally placed semicylindrical reaction vessel having a heat transfer surface formed by the outer wall and the agitator shaft and having two to four inlet ports for the starting material and one outlet port for the product.

DETAILED DESCRIPTION OF THE INVENTION

According to one feature of the present invention, an ordinary reaction vessel of the above type may be used instead of a specially devised one. The preprocessing steps such as pre-heating and melting urea are also unnecessary. As heat transfer medium, Santtherm (prepared by the Monsanto Company, U.S.A.), HTS (heat transfer salt, consisting of 40 wt. percent of $NaNO_2$, 7 wt. percent of $NaNO_3$ and 53 wt. percent of $KNO_3$) and Dowtherm oil (prepared by The Dow Chemical Company, U.S.A.) may be employed, but other heat transfer media may also be used within the scope of the present invention. The heat transfer surfaces may be provided as conventionally by the wall surface of the vessel, the agitator shaft or a coil immersed in the reaction product. Thus, the heat transfer medium does not come into direct contact with the reaction mixture.

In the present method, urea is supplied continuously as starting material and the reaction is also carried out continuously, but the product is taken out continuously or intermittently, as the occasion may so demand.

According to an essential feature of the present invention, the heat transfer surface is maintained at a temperature higher than 340°C, preferably between 340°C and 360°C. When the temperature of the heat transfer surface falls below 340°C, the reaction mixture may be deposited as a thin film on the heat transfer surface, even if the reaction product is stirred and kept in a fluid state. The film thus formed may become thicker and lower the heat transfer efficiency or retard the agitation and the further progress of the reaction. When the temperature of the heat transfer surface is higher than 340°C, the transfer surface is always clean with the metallic surface exposed to the reaction mass. Even if the reaction product should be deposited on the heat transfer surface, it may be scaled off immediately, possibly because cyanuric acid formed at the heat transfer surface is vaporized and removed at the temperature of 340°C, or a gap is formed between the heat transfer surface and the deposited film at such temperature, although the mechanism for such phenomenon is not known in great detail. Vaporization loss may be suppressed to the minimum because cyanuric acid vaporized on the heat transfer surface may be brought immediately into contact with the reaction product contained in the vessel and kept at a sufficiently low temperature of 220°C to 280°C. The temperature of the heat transfer surface higher than e.g. 360°C should however be avoided in view of the loss of urea and cyanuric acid and the closure of the discharge pipe.

Thus, if the heat transfer surface is maintained at a temperature between 340°C and 360°C, the reaction may be carried out under smooth stirring and heating with an improved yield of cyanuric acid.

According to another essential feature of the present invention, the reaction mass should be maintained at a temperature higher than 220°C, preferably between 220°C and 280°C. Especially, any local point of the reaction mass should not be lower than 220°C. The starting material is supplied without advance treatment of any kind and hence it is maintained at an ambient temperature. It is not therefore required by the present invention that each particle of urea should be maintained at higher than 220°C immediately after delivery thereof into the reaction vessel, which is, indeed, a difficult operation to perform. It is however required by the present invention that any local point of the reaction mass should be maintained at the specified temperature in the sense that the indication of the thermometer inserted in any desired zone of the reaction mass should always be higher than 220°C. When the reaction vessel has only one inlet port for the raw material, the latter is charged at the low temperature from only one place and hence the temperature of the reaction mass may be lowered locally in spite of intense agitation. Preferably, the starting material is sprayed into the vessel from a number of supply ports, but it is not practically advantageous because of the overly complicated structure of the reaction vessel. Should the starting material be sprayed from a number of inlet ports, if a considerable quantity is supplied relative to the quantity already contained in the reaction vessel, the temperature of the reaction mass may be decreased locally due to the lowered heat transfer velocity and the shortage in the absolute quantity of the transferred heat. In general, two to four supply ports for the starting material are preferred for the commonly used reaction vessels, depending on the structure of the reaction vessel, the stirring speed, the temperature of the heat transfer medium, the quantity of the reaction mass, the supply quantity of the starting material and other related factors.

According to a further essential feature of the present invention, the mean residence time for the reaction mass, given as a ratio of the quantity of the reaction mixture in the vessel to the supply rate of the starting material, should be longer than 2.5 hours. The mean residence time shorter than 2.5 hours is undesirable for industrial application because the urea conversion percentage or the yield of cyanuric acid is lowered and, besides, an excess quantity of mineral acid would be consumed in the subsequent refining step. In addition, should the mean residence time be shorter than 2.5 hours, it is difficult to continue the reaction under fixed and stable conditions because of the increased supply rate of urea to the reaction mixture and the resulting tendency for the reaction mixture to agglutinate or form pellets.

The crude cyanuric acid is obtained in accordance with the present method in the form of powder or particles or the mixture thereof, but the status of the obtained product does not affect the progress of agglutination, pelletization or the reaction appreciably. As the crude cyanuric acid obtained by the inventive method contains ammeline, ammelide and other by-products, it may be subjected to hydrolysis, refining and filtration in a known manner to give pure cyanuric acid.

The present method is carried out with use of a commonly employed heat transfer medium heated type stirring vessel and without the necessity of performing any special preprocessing of the starting material. The final product may be obtained efficiently with a high yield because the reaction mixture does not become agglutinated or solidified during the reaction and hence the difficulty in operating the agitator or the troubles in the heat transfer performance may be avoided.

Below, typical numerical examples of the present invention will be explained in detail in connection with a comparative example for better understanding of the present invention.

The heat transfer medium heated type stirring vessel used in the following examples is a horizontal type device of a semicylindrical shape and the heat transfer surface of the vessel is provided by the outer wall and the agitator shaft. The heat transfer surface has an area of 10 m². The agitator is horizontally placed and rotates at 20 r.p.m. The vessel has a capacity of 500 kg and is provided with four inlet ports for the starting material, one outlet port for the product and separate exhaust ducts, with inlet and outlet ducts for the heat transfer medium.

EXAMPLE 1

Urea was supplied under agitation from the four inlet ports into the reaction vessel at a rate of 170 kg/hr. The temperature of the heat transfer medium and that of the reaction mass were maintained at 350°C. and 230°C, respectively. The product was taken out at a rate of 90 kg/hr after a mean residence time of 2.9 hours. The reaction was continued under stable conditions because the heat transfer surface was always clean with the metallic surface being exposed and the reaction product was not agglutinated or pelletized during the reaction. The crude cyanuric acid thus obtained contained 4 percent of urea, 2 percent of ammeline, 13 percent of ammelide and 81 percent of cyanuric acid. The cyanuric acid thus obtained was subjected to refining through hydrolysis and cyanuric acid was obtained at a yield of 71 percent of the supplied urea. Most of the loss in the yield represents the quantity of urea that is vaporized during the reaction and can be recovered by way of the exhaust pipe.

When the urea was supplied at a rate of 190 kg/hr, the temperature of the reaction mass was reduced suddenly. The reading of the thermometer mounted near the supply port was 180° to 190°C while the thermometers mounted in other places read 220°C. Agglutination of the reaction mass occurred under this condition.

On the other hand, while the reaction was continued under stable conditions in accordance with the Example 1, the supplied quantity of urea was reduced to 110 kg/hr. and the temperature of the reaction mass was gradually lowered by reducing the quantity of the circulated heat transfer medium. The outlet temperature of the heat transfer medium was kept at 350°C. When the temperature of the heat reaction mass was lowered to 190°C, the reaction mass was agglutinated as a whole, and the operation was hindered completely.

On the other hand, while the reaction was continued under stable conditions in accodance with the Example 1, urea was supplied from only one supply port and at a reduced supply rate of 100 kg/hr. The temperature of the reaction mass at the inlet port was lowered rapidly to 180°C in 10 minutes. The reaction mass was agglutinated and the reaction hindered completely. The readings on the remaining thermometers were 240°C, 250°C or thereabout.

EXAMPLE 2

With use of the same reaction vessel as employed in the preceding Example 1, urea was supplied from the four inlet ports at a supply rate of 185 kg/hr. and the product was taken out at a rate of 96 kg/hr. The temperature of the heat transfer medium and that of the reaction mass were maintained at 360°C and 230°C, respectively. The reaction was carried out with a mean residence time of 2.7 hours. In this case, the reaction could be continued smoothly and stably as in the preceding Example 1. The crude cyanuric acid thus obtained contained 3 percent of urea, 2 percent of ammeline, 14 percent of ammelide and 81 percent of cyanuric acid. The crude acid was subjected to refining through hydrolysis to refined cyanuric acid with a yield of 69 percent.

COMPARATIVE EXAMPLE

Using the same reaction vessel as in the preceding Examples, urea was supplied from four places at a rate of 110 kg/hr. and the product was taken out at a rate of 60 kg/hr. The temperatures of the heating medium and the reaction mixture were maintained at 330°C and 230°C, respectively. The reaction was carried out with a mean residence time of about 4.5 hours. In this case, the reaction could be continued under stable conditions, but more than about one half the heat transfer surface was covered with the deposited reaction mass to a thickness of several millimeters.

When the urea supply was increased to 130 kg/hr, the temperature of the reaction mixture was rapidly lowered to 190° to 22°C and the reaction mixture started to agglutinate.

In the above Examples 1 and 2 and the Comparative Example, the temperature of the heat transfer medium is indicated by the outlet temperature of the heat transfer medium. Since the inlet temperature is higher by several degrees C than the indicated temperature, the temperature of the heat transfer surface is comprised between the above-mentioned inlet and outlet temperatures.

What is claimed is:

1. A method of producing cyanuric acid by heating urea in bulk comprising supplying urea continuously under agitation into a reaction vessel, the heat transfer surface of which is maintained at a temperature higher then 340°C, said vessel being equipped with an agitator and heated indirectly by a heat transfer medium, maintaining the reaction mixture permanently at a temperature higher than 220°C in any local point, and carrying out the reaction with a mean residence time of over 2.5 hours with heating and agitating, wherein said heat transfer medium does not come into direct contact with said reaction mixture.

2. The method of claim 1 wherein the heat transfer surface of the reaction vessel is maintained at a temperature from 340°C to 360°C and the reaction mixture is maintained at a temperature from 220°C to 280°C.

3. The method of claim 2 wherein the urea is supplied through two to four supply ports into said reaction vessel.

4. A method for producing cyanuric acid with use of a horizontally placed semicylindrical reaction vessel equipped with an agitator and heated indirectly by a heat transfer medium, said reaction vessel having a heat transfer surface formed by the outer wall and the agitator shaft and having two to four inlet ports for the starting material with one outlet port for the product, wherein urea is reacted in said vessel under heating and agitation with a mean residence time of over 2.5 hours while supplying urea continuously and under agitation into said vessel through said inlet ports and maintaining the temperature of the heat transfer surface at 340°C to 360°C and that of the reaction mixture in any local points thereof at 220°C to 280°C permanently, and wherein the product is taken out continuously or intermittently by way of said outlet port of the reaction vessel.

* * * * *